Figure 1:
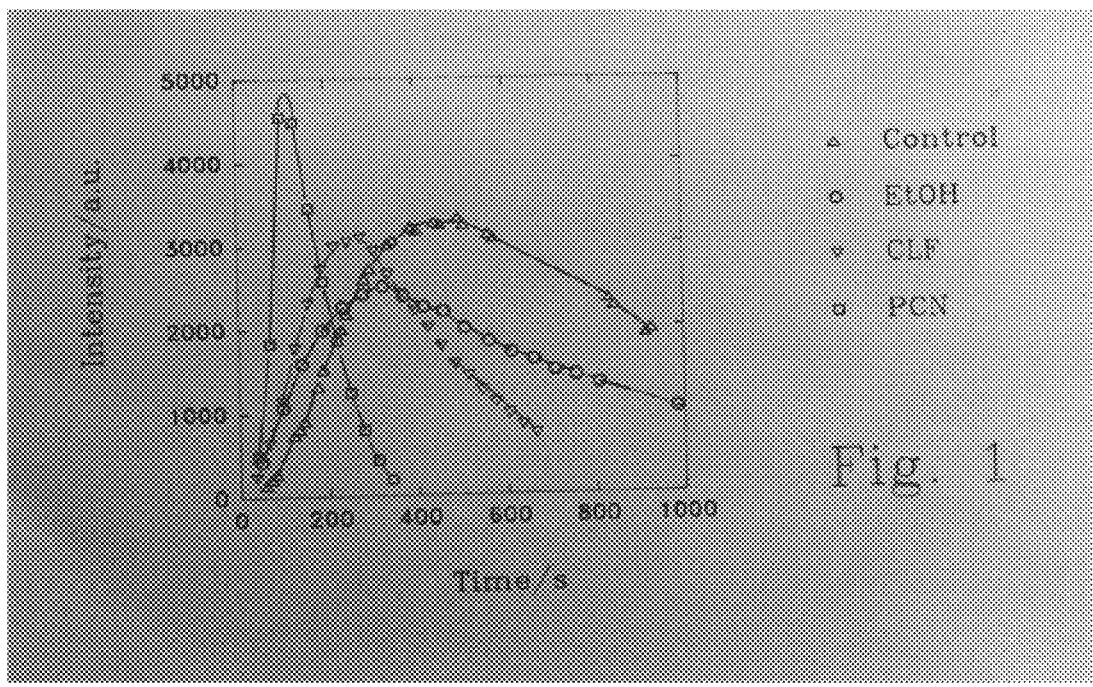

United States Patent [19]
Paolini et al.

[11] Patent Number: 5,981,548
[45] Date of Patent: Nov. 9, 1999

[54] N-HYDROXYPIPERIDINES AS SUPEROXIDE RADICALS SCAVENGERS

[75] Inventors: Moreno Paolini, Pappiana; Gian Franco Pedulli, Bologna, both of Italy

[73] Assignee: Moreno Paolini, Pappiana, Italy

[21] Appl. No.: 08/836,614

[22] PCT Filed: Nov. 15, 1994

[86] PCT No.: PCT/EP94/03785

§ 371 Date: Jul. 7, 1997

§ 102(e) Date: Jul. 7, 1997

[87] PCT Pub. No.: WO96/15110

PCT Pub. Date: May 23, 1996

[51] Int. Cl.$^6$ ...................... A61K 31/445; C07D 211/94
[52] U.S. Cl. .......................... 514/316; 546/188; 546/216; 546/242; 424/9.2
[58] Field of Search ...................... 546/188, 216, 546/242; 514/327, 315, 316; 424/9.2

[56] References Cited

U.S. PATENT DOCUMENTS

| | | | |
|---|---|---|---|
| 4,665,185 | 5/1987 | Winter et al. | 546/184 |
| 5,064,883 | 11/1991 | Behrens et al. | 524/95 |
| 5,185,448 | 2/1993 | Odorisio et al. | 546/186 |

OTHER PUBLICATIONS

Carlsson, D.J. et al.: Hindered amines as antioxidants in UV exposed plymers. Polym. Sci. Technol. vol. 26, pp. 35–47, 1984.

Jurkiewicz, B.A. et al.: Effect of topically applied tocopherol on ultraviolet radiation–mediated free radical damage in skin. J. Invest. Dermatol., vol. 104, pp. 484–488, 1995.

Masaki, H. et al.: Detection of hydrogen peroxide and hydroxyl radicals in murine skin fibroblasts under UVB irradiation. Biochem. Biophys. Res. Commun. vol. 206, pp. 474–479, 1995.

Dalle Carbonare, M. et al.: Skin photosensitizing agent and role of reactive oxygen species in photoaging. J. Photochem. Photobiol. B:Biol., vol. 14, pp. 105–124, 1992.

Masaki, H. et al.: Generation of active oxygen species from advanced glycation end–products ( AGE ) under ultraviolet light A ( UVA ) irradiation. Biochem. Biophys. Res. Commun. vol. 235. pp. 306–310, 1997.

Cerutti, P.A.: Prooxidant states and tumor promotion. Science, vol. 227, pp. 375–376, 1985.

Kubow,S.: Routes of formation and toxic consequences of lipidic oxidation products in foods. Free Radical Biology & Toxicol. vol. 12, pp. 63–81, 1992.

Sevenian, A. et al.: Mechanisms and conservation of lipidic peroxidation in biological systems. Ann. Review Nutrition. vol. 5, pp. 365–390, 1985.

Kanner, J. et al.: Catalytic "free" iron ions in muscle foods. J. Agric. Food Chem., vol. 36, pp. 413–415, 1988.

Begin, M.E.: Fatty acids, lipid peroxidation and diseases. Proc. Nutr. Soc., vol. 49, pp. 261–267, 1990.

*Primary Examiner*—John Kight
*Assistant Examiner*—Charanjit S. Aulakh
*Attorney, Agent, or Firm*—Rockey, Milnamow & Katz, Ltd.

[57] ABSTRACT

Compositions including as active ingredients cyclical hydroxylamines of the formula (I) are usefull for treating and preventing pathologies concerned with over production of oxygen-centered free radicals and as foodstuff and cosmetic additives for preventing lipoperoxydation.

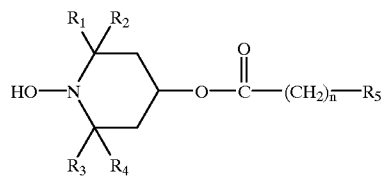

(I)

11 Claims, 4 Drawing Sheets

N-HYDROXYPIPERIDINES AS SUPEROXIDE RADICALS SCAVENGERS

This application is a 371 of PCT/EP 94/03785, filed Nov. 15, 1994, now WO 96/15110 published on May 23, 1996.

TECHNICAL FIELD

The present invention relates to chemical compounds, the synthesis process thereof, to pharmaceutical and cosmetic compositions comprising said compounds, and to the use of said compounds as a diagnostic means and as additives for food.

BACKGROUND ART

More specifically, this invention relates to certain cyclical hydroxylamines, to the synthesis thereof, and to compositions containing said compounds, such as pharmaceutical compositions adapted to the therapeutical use in the treatment of all those pathologies concerned with production, or an excess production, of oxygen-centered free radicals; the invention further relates to cosmetic compositions having anti-free radical activities, to the use of said cyclical hydroxylamines as additives to avoid rancidity of foodstuffs and deterioration of cosmetic products, and as a diagnostic means (marker) to reveal the status (of oxidative and/or inductive stress) at high carcinogenic risk and held responsible of other pathologies.

A number of normal and/or pathological processes are known in the course of which the formation of reactive radical species takes place. As a result of the general position of oxygen in aerobic organisms and also in human beings, as well as its high availability in accepting single electrons, the oxygen-centered free radicals very often are the protagonists of cellular reactions in physiopathology.

A plurality of conditions are also known to be capable of increasing the radical production within cells, such as a change in oxygen tension (in hyschemia, riperfusion, shock, transplants), lack of A, E vitamins, aging, administration of drugs of certain classes (halogen-alcanes, chemotherapy drugs, carcinogenic drugs, ethanol, paracetamol, etc.). There are also a plurality of conditions which increase the oxygen production in extra-cellular spaces, such as conditions arising from acute inflammatory states (infections, burns), chronic inflammatory states (rheumatoid arthritis, ulcerative colites, vasculites); immune disorders, immunocomplex pathologies, etc.

Moreover, antioxidant enzymes are also known for use as pharmacological agents and particularly it is known to use superoxide dismutase (SOD) in order to limit the excess production of said free radicals. This enzyme, of endogenous type, is capable of transforming the superoxide anion into oxygen and hydrogen peroxide, which will be later eliminated by catalase and peroxidase. This solution however has got quite a few problems arising from the poor stability of said enzyme the half life of which, once injected intravenously, ranges from about 6–8 minutes for the most commonly used form (Cu, Zn-SOD) to a few hours (Mn, PEG-SOD). Importantly, said enzymes, both native or modified, are obtained by cloning human genes and have activities modified by site-specific mutagenesis, which however involves high production costs.

A further disadvantage relevant to the use of said enzyme is the impossibility of achieving suitable concentrations of enzyme in the body areas where protection is required. To eliminate the above drawback, it is necessary to administer said enzyme in high and discontinuous dosages. However, since administration is intravenous, it is easy to understand that this methodology is not convenient.

Further, SOD, because of its large molecular dimensions, will not enter the intracellular environment, unless phagocytized by endothelial cells.

Although in order to obviate said problem, an attempt has been made to encapsulate the enzyme in specific vesicles having lipidic nature (the so-called 'liposomes') so as to make the passage easier through the double lipoproteinic layer of biological membranes, further problems have arisen related to the bio-technological process of realization and also to the difficulty of said liposomes to reach certain body areas through thin capillaries, in which the high blood flow rate do not allow a proper absorption of said liposomes into the specific tissue.

It is also known to coat liposomes with specific antibodies which will recognize the tissue where protection is required. This however introduces new limitations due to the high cost involved in preparing said antibodies.

It is also known to employ metal chelates, such as Mn; but besides dissociating very easily, said chelates have the further disadvantage of catalyzing undesirable redox processes in cells and also exhibit high affinity to proteins and amino acids.

A further disadvantage in the use of metal chelates is that said chelates may lose their activity upon binding to plural cellular components.

From scientific literature there is known oxane (2-ethyl-2,5,5-trimethyl-3-oxazolidonoxyl) which is currently the molecule with the best characteristics for acting as a 'capturing agent' for superoxide.

Said oxanic derivative however has the drawback of being poorly lipophilic, which does not allow it, when administered, to readily pass through the double lipoproteinic layer of the biological membranes. In addition said derivative exhibits high synthesis costs.

DISCLOSURE OF THE INVENTION

It is an object of the invention to provide a class of compounds to solve the above mentioned problems, and particularly to provide a class of compounds having a high capability of acting as a capturing agent for superoxide anion and also having high lipophily allowing said compound to easily pass through the double lipoproteinic layer of the biological membranes, obtaining thereby a high concentration of active substance in the body area where anti-radical protection is required.

It is another object of the invention to provide a class of compounds which, besides having a high capability of capturing the superoxide anion, have small areas, are stable and are easily produced in large amounts.

Not the least object of the invention is to provide a molecule which may be used for producing a composition adapted to be employed as a diagnostic means to reveal the individual inductive status at high carcinogenic risk, as well as the individual oxidative status, and the detection thereof is not intrusive for the patient.

Still another object of the invention is to provide a class of molecules which can be used for producing a composition which, when added to foodstuffs, prevents them to become rancid, providing at the same time a protection 'anti-free radicals' effect inside the organism which said composition is administered to.

Yet another object of the invention is to provide a class of molecules which can be used for producing such a composition that added to cosmetic products, prevents the deterioration thereof and also exhibits an anti-free radical protective effect.

With the foregoing and other objects in view, there is provided a compound of the formula (I):

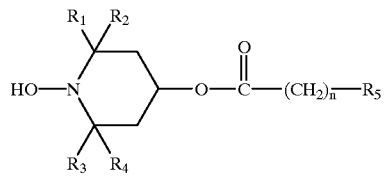

wherein $R_1$, $R_2$, $R_3$, $R_4$ are independently selected from:

hydrogen, alkyl of from one to twelve carbon atoms, preferably of from one to six carbon atoms and more preferably of from one to three carbon atoms, alkenyl of from two to twelve carbon atoms, preferably of from two to six carbon atoms and more preferably of from two to three carbon atoms, alkynyl of from two to twelve carbon atoms, preferably of from two to six carbon atoms and more preferably of from two to three carbon atoms, or $R_1$ and $R_2$ together are tetramethylene or pentamethylene;

$R_5$ is hydrogen, alkyl of from one to twelve carbon atoms, preferably of from one to six carbon atoms and more preferably of from one to three carbon atoms, cycloalkyl of from three to eight carbon atoms, alkenyl of from two to twelve carbon atoms, preferably of from two to six carbon atoms and more preferably of from two to three carbon atoms, alkynyl of from two to twelve carbon atoms, preferably of from two to six carbon atoms and more preferably of from two to three carbon atoms or

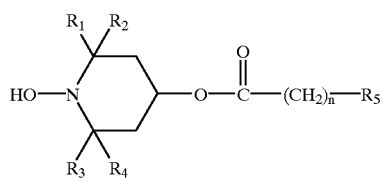

wherein $R_1$, $R_2$, $R_3$, $R_4$ are as defined above and n preferably is an integer of from one to thirty, more preferably of from two to fortheen and more preferably of from six to ten.

A group of compounds which are illustrative of the present invention are compounds of the formula:

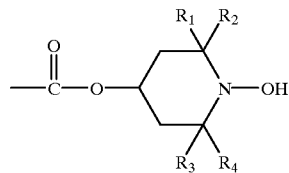

wherein $R_1$, $R_2$, $R_3$, $R_4$ are an alkyl of from one to three C $R_5$ is

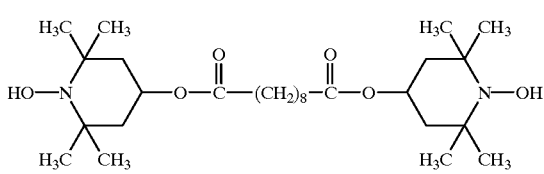

wherein $R_1$, $R_2$, $R_3$, $R_4$ are an alkyl of from one to three C and n is an integer of from six to ten, and in particular a compound particularly preferred having the formula:

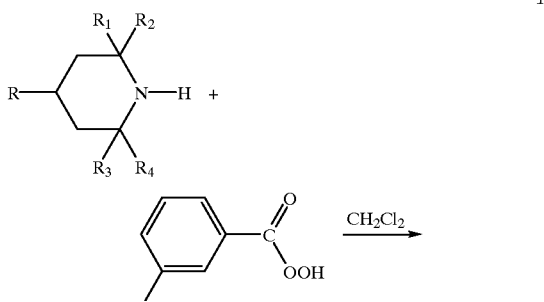

and having the name: bis (1-hydroxyl-2,2,6,6-tetramethyl-4-piperidinyl) decandioate.

The compounds according to this invention are preferably. prepared by means of the general synthesis process detailed in Reaction Sequence 1, as follows:

1

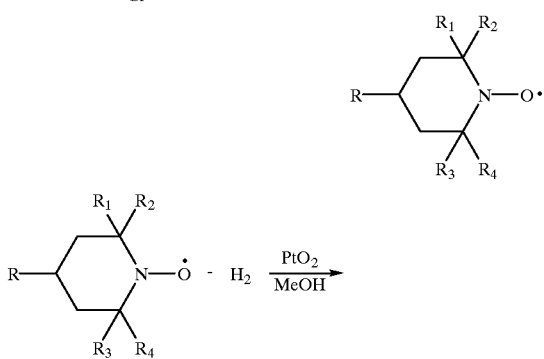

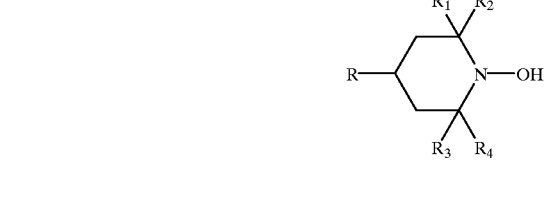

With reference to Reaction Sequence 1, the desired cyclic hydroxylaminic starting compound is first changed to the corresponding N-oxyl derivated by reaction with m-chloroperbenzoic acid. The N-oxyl derivative is dissolved in methanol and subjected to catalytic hydrogenation using PtO$_2$ (Pt as a catalyst) to produce the cyclic 2,2,6,6-tetrasubstituted hydroxylamine in accordance to this invention.

It is also an object of this invention to provide a method for preparing a compound of said formula (I).

Said preparation method comprises:

a) reacting a compound of the formula

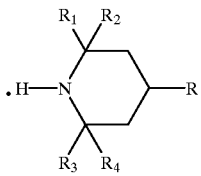

wherein R is

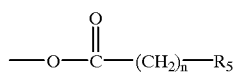

R$_1$, R$_2$, R$_3$, R$_4$ each are:
hydrogen;
alkyl of from 1 to 12 carbon atoms, preferably 1 to 6 carbon atoms, more preferably 1 to 3 carbon atoms;
alkenyl of from 2 to 12 carbon atoms, preferably 2 to 6 carbon atoms, more preferably 2 to 3 carbon atoms;
R$_5$ is hydrogen,
alkyl of from 1 to 12 carbon atoms, preferably 1 to 6 carbon atoms, more preferably 1 to 3 carbon atoms;
cycloalkyl, preferably with 3 to 6 carbon atoms,
alkenyl of from 2 to 12 carbon atoms, preferably 2 to 6 carbon atoms, more preferably 2 to 3 carbon atoms;
alkinyl of from 2 to 12 carbon atoms, preferably 2 to 6 carbon atoms, more preferably 2 to 3 carbon atoms;

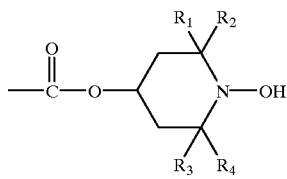

wherein R$_1$, R$_2$, R$_3$, R$_4$ are as defined above,
n is an integer between 1 and 30, preferably between 2 and 14, more preferably between 6 and 10;
with a m-chlorobenzoic acid in a solvent to obtain an N-oxyl derivative of the formula

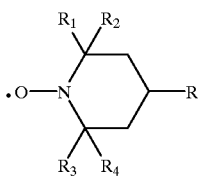

wherein R$_1$, R$_2$, R$_3$, R$_4$ are as defined above for step a), b) subjecting the resulting compound of step a) to hydrogenation to give compound

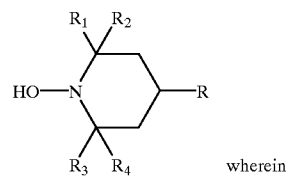

wherein

R$_1$, R$_2$, R$_3$, R$_4$ are as defined above.

The term "alkyl of from one to twelve carbon atoms" denotes a substituent group derived from a saturated hydrocarbon by removal of a single hydrogen atom. The term includes methyl, ethyl, n-propyl, iso-propyl, n-butyl, sec-butyl, iso-butyl, tert-butyl, and the various isomeric forms of pentyl, hexyl, eptyl, octyl, nonyl, decyl, undecyl and twelvyl. Likewise, the terms "alkenyl of from two to twelve carbon atoms" and "alkynyl of from two to twelve carbon atoms" denote substituent groups derived, respectively, from alkene or alkyne hydrocarbons by the removal of a single a hydrogen atom. These terms include ethenyl, ethynyl, propenyl, propynyl, and similar branched and unbranched unsaturated hydrocarbon groups of up to twelve carbon atoms.

The term "cycloalkyl of from three to eight carbon atoms" denotes saturated carbocyclic rings such as cyclbpropyl, cyclobutyl, cyclopentyl, cyclohexyl, as well as alkyl substituted carbocyclic rings containing up to eight carbon atoms such as methyl-, dimethyl-, and ethylcyclohexyl.

The compounds of the type described hereinabove are similar to those known from U.S. Pat. No. 4,691,015.

The compounds hereinabove described are therefore the pharmacological agents chosen to capture the oxygen free radicals which are associated to a number of different human pathologies such as phlogistic processes, alcoholic hepatopathy, liver transplants, metabolic sicknesses, alterations in lipoproteins, lung pathologies, haematologic disorders, glomerule pathology, spermatozoa pathology, coronary atherosclerosis, hyperbaric damage affecting the central nervous system, radiation damage, DNA damage by genotoxins, oxidative polymorphisms, inductive status, etc.

According to another aspect, the present invention provides both pharmaceutical compositions and the use of the above mentioned compounds for preparing pharmaceutical compositions for treating symtoms due to excess production of superoxide radical.

Said pharmaceutical compositions are particularly useful in preventing degenerative oxidation processes which take place in mammals, by means of administration to the subject who needs to be treated, of at least a compound as above set forth in combination with a pharmaceutically acceptable carrier.

In therapeutic use as treating agents for pathologies associated with an excess production of superoxide radicals, compounds according to this invention are administered to patients at dosage levels preferably in a range of 0.02 to 200 mg/kg per body weight, and more preferably in a range of 0.5 to 30 mg/kg per body weight, for single or multiple administration a day.

The specific dosages used however may vary according to the patient needs, the severity of the pathologies requiring treatment, and the activity of the compound to be used. The determination of an optimum dosage to be administered in each particular situation is within the choice possibilities of those skilled in the art.

For manufacturing pharmaceutical compositions comprising at least one of the compounds according to the invention, pharmaceutically acceptable carriers are usable, both in powder and liquid form.

Solid preparations will include powders, tablets, pellets, capsules, cachets and suppositories.

A solid carrier can consist of one or more substances capable of acting also as dilution, flavouring, solubilizing agents, lubricants, suspension agents, binders, or disaggregating agents; it may also be encapsulated material. As to the powders, the carrier consists of a finely divided solid which is blended with at least an active compound. In the tablets the active ingredient is in admixture with a carrier having the requisite binding characteristics, in suitable proportions and compacted to the desired size and shape.

Powders and tablets will contain preferably 5 to about 70% by weight of the active ingredient.

Suitable carriers are mainly represented by magnesium carbonate, magnesium stearate, talc, lactose, sugar, pectine, dextrine, corn starch, methylcellulose, sodium carboxymethylcellulose, low melting point waxes, coconut butter, and the like.

Also dosage forms suitable for oral administration, tablets, powders, cachets and capsules may be used.

Preparations in the liquid form include solutions adapted to parenteral or oral administration, or suspensions and emulsions adapted for oral administration. By way of an example of liquid preparations adapted to parenteral administration, both sterile aqueous solutions of the active ingredient and sterile solutions of the active ingredient in solvents, such as water, ethanol or propylene glycol may be mentioned.

Sterile solutions may be prepared dissolving the active ingredient in the desired solvent system, passing then the resulting solution through a membrane filter for the alternate sterilization of said solution in a previously sterilized solvent, under sterile conditions.

Aqueous solutions intended for oral administration may be prepared by dissolving the active ingredient in water and adding suitable coloring, flavoring agents, stabilizers, and bulking agents in the requisite amounts.

Aqueous suspensions for oral use may be prepared by dispersing in water the finely divided active ingredient together with a viscous material such as natural or synthetic rubbers, resins, methylcellulose, sodium carboxymethylcellulose, and other suspending agents known in the art of pharmaceutical formulations.

Preferably, the pharmaceutical formulation will be in the form of single dose units, weighting preferably 1 to 100 mg. In that form, the preparation is partitioned in unit doses containing suitable amounts of the active ingredient. Said single dose unit may be composed of a packed preparation including tablets, capsules and powders in vials and bottles.

Compounds in accordance with this invention are also usable for manufacturing a composition for use as a diagnostic means (marker); particularly said compounds may be used to highlight the carcinogenic level of risk in a human being. Said use of one of the hydroxylaminic compounds of this invention and particularly of bis(1-hydroxyl-2,2,6,6-tetramthyl-4-piperinidyl)decandioate involves the administration of said compound with a dosage preferably in the range of 0.5 to 30 mg/kg, and the subsequent detection of the nitroxide formed in the organism of the subject being treated. Said nitroxide is in a form easily detectable by EPR analysis of urine contents. A detected high level of nitroxide is an indication of high carcinogenic risk.

Compounds according to this invention may also be used for the production of an additive composition, alone or in admixture with other antioxidant substances, particularly adding an amount of said hydroxylaminic compound in accordance with this invention, preferably comprised in a range of 0.001% to 2% w/w of the food to be treated with said additive according to the rules in force. The substance according to the invention is particularly useful to prevent rancidity of foodstuffs which easily undergo oxidation, such as milk and its derivative products, cheese, oils and the like without modifying the organoleptic properties thereof. In addition, said substance is not toxic to human organism, performing on the contrary a further protective function, upon assimilation.

Finally, compounds according to this invention may also be used for preparing an additive composition, alone or in admixture with other substances, both antioxidant and non-antioxidant, particularly with the addition of a hydroxylaminic compound according to this invention in a quantity of 0.001% to 2% w/w of the cosmetic product to be treated with said additive. Substances according to this invention are particularly useful to prevent oxidative deterioration of cosmetic products which easily undergo oxidation, such as creams, oils, gels etc.; said substance being non toxic to humans, performing on the contrary a further anti-free radical protective action upon absorption of the skin.

The following example will allow one skilled in the art to practice the invention. Thus, it is illustrative of this invention and has been accluded only by way of an indication and not a limitation.

EXAMPLE 1

Synthesis of the N-oxyl Derivative of 2,2,6,6-tetramethyl-4-Piperidine:

8.4g (0.075 mol) 2,2,6,6-tetramethyl-4-piperidine sebacate (Tin 770) was dissolved in dichloromethane, 30 ml. To the thus obtained solution, m-chloroperbenzoic acid, 14.7 g (0.07 mol), in dichloromethane 170 ml was slowly (in about 4 hours) added under stirring, at room temperature.

The obtained mixture was stirred for 20 hours at room temperature, cooled to about 0° C. and added with a 2N aqueous NaOH solution.

The organic phase was separated, washed with $H_2O$ 2×60 ml, dried over anhydrous $Na_2SO_4$, filtered and evaporated at 50° C. and 24 mbars. The obtained residue was crystallized from methanol, filtered and dried in an oven at 45° C. in vacuo (1.3 mbars) to give a solid, m.p. 99–101° C.

Analysis % for $C_{28}H_{50}N_2O_6$; Calculated: C=65.85; H=9.87; N=5,49; Found: C=65.49; H=9.87; N=5,45;

Synthesis of the Hydroxylamine Derivative of 2,2,6,6-tetramethyl-4-piperidinil:

5.1 g (0.01 mol) N-oxyl derivative of 2,2,6,6-tetramethyl-4-piperidil sebacate was dissolved in methanol, 30 ml and added with $PtO_2$, 0.05 g. The solution was placed into a Parr hydrogenator and hydrogenated at room temperature under a pressure of 1.02 bars. The reaction was completed in 4 hours. The solution was filtered, evaporated at 60° C. under 24 mbars.

The obtained residue was crystallized from methane.

After drying in an oven (1.3 mbars) a product is obtained having m.p. 126–127° C.

The antioxidant activity of the compounds according to the invention will become more evident from the description of the following examples which aim at measuring the capability of cyclic hydroxylamines in accordance with this invention, to act as 'superoxide capturers', using a particular enzyme system composed of P450 cytochrome monoxygenasic system—known to be able of producing the superoxide radical anion.

Cytochrome P450 is a large gene family of haemoproteins responsible for the metabolism of a variety of xenobiotics.

These proteins are considered to exhibit different types of activities, such as monooxygenases, peroxidases, reductases and oxidases.

It has been suggested that self-oxidation of the oxycytochrome complex P450 is a potential source of superoxide and of the related radicals thereof. Under particular conditions of environment (cigarette smoke, alcohols, etc.) and work (thinners, PCB, etc.) exposition, pharmacological treatment (barbiturates, chlorophilate, niphedipine, etc.) or in certain polymorphisms, an increase in production of oxygen centered radicals is possible, which may play a role in a number of pathologic processes.

As an example, we report the results obtained by using the bis(1-hydroxyl-2,2,6,6-tetramthyl-4-piperinidyl) decandioate as the hydroxylamine.

Male Swiss Albino mice strain aged 7–8 weeks were maintained on a standard supplemented laboratory diet of 'Pellet Nossan' (available from the Nossan Company in Milan, Italy) prior to treatment. Six inducers specific to different P450 isoforms were injected singularly at equimolar doses (0.35 mmcl/kg) i.p., β-naphtoflavone(BNF isoforms P450IA1), isosafrol (IS, IA2), sodium phenobarbital (PB, IIB1), pregnenolone-16-α-carbonitrile (PCN, IIIA), clofibrate (CL, IVA), or ad libitum (15%, v/v) ethanol (ETOH, IIE1) for three weeks. Mice were fasted for 16 hours prior to sacrifice, then killed by cervical dislocation after stunning by rotation. Livers were removed aseptically, homogenized with a Potter Elvehjem homogenizer (4 ml/g of the organ weight) in a 0.01M $Na^+/K^+$ phosphate buffer (pH 7.4) containing KCl 1.15% (w/v) and 1 mM EDTA, then centrifugated 20 min at 9,000 g. The thus obtained postmythocondrial supernatant (S9 fraction) was centrifugated 60 min at 105,000×g. Pellets were washed with a 0.01M $Na^+/K^+$ phosphate buffer (pH 7.4) containing 1 mM EDTA, then centrifugated again at 105,000×g to give the final mycrosomial fraction. The thus obtained final pellets were risuspended in a $Na^+/K^+$ phosphate buffer (pH 7.4) containing and 1 mM EDTA and 20% glycerol (w/v). The subcellular fractions were immediately frozen in liquid nitrogen (−196° C.) and stored at −80° C. before use. The purified mycrosomes were incubated directly in the RPR sample tubes at 37° C. in a $Na^+/K^+$ phosphate buffer (pH 7.4) in the presence of 1 mM hydroxylamine, 0.06 mM $NADP^+$, 3.33 mM glucose-6-phosphate, 4 mM $MgCl_2$ and 0.93 U/ml dehydrohenase glucose-6-phosphate. After thorough stirring, the sample was immediately introduced inside the EPR cavity and the three line spectrum ($a_N$=15.50 G, g=2.0062) of the formed nitroxide was recorded at regular time intervals. The content in P450 was determined by recording the differential spectrum of the reduced form related to CO with respect to the non-complexed form. A non-transformed murine hepathocellular line (c2.8) recently isolated from livers of fetal mice, by means of co-cultivation with lethally irradiated cells of the human promonocytic cell line (CM-S).

Figure 2:
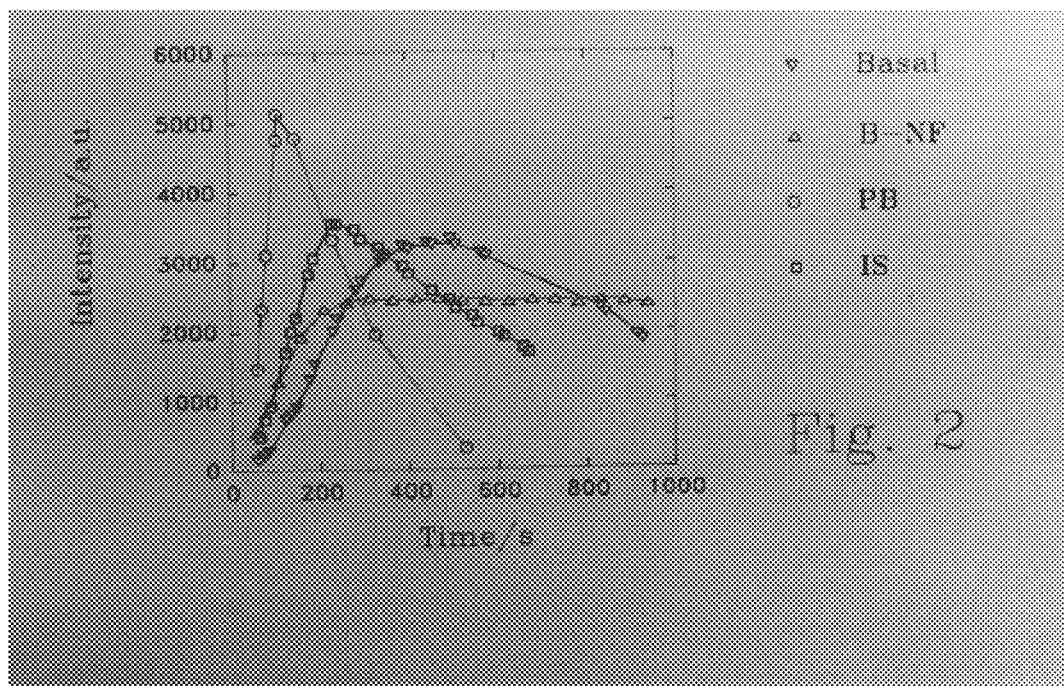
Figure 3:
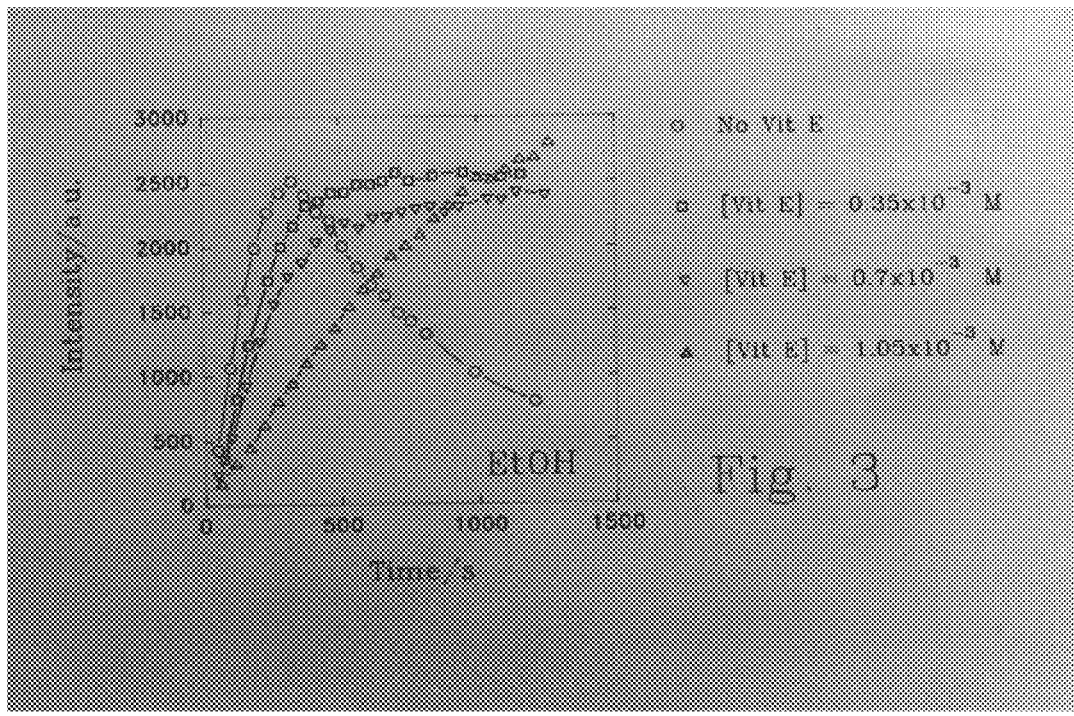
Figure 4:
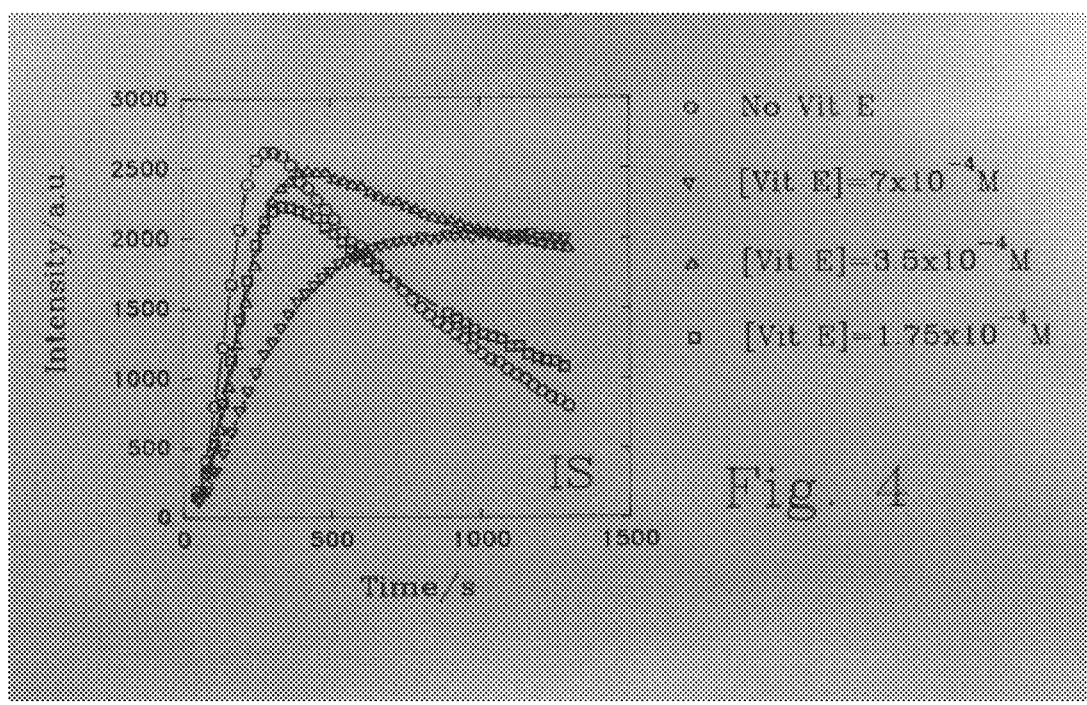

The time evolution of the intensity of the EPR spectrum of the stable nitroxide radical formed by superoxide oxidation of the hydroxylamine, is reported in FIGS. 1 and 2 for six P450 inducers. In every case the intensity reaches a maximum and then decreases again. The initial rate of formation of the radical is higher with any inducer than with the control. FIGS. 3 and 4 report the results of experiments similar to the previous ones, performed in the presence of α-tocopherol (Vitamin E). Under these conditions we observed:
 i) a decrease of the rate of formation of the nitroxide;
 ii) a progressive reduction of the rate of decay of the nitroxide with increasing Vitamin E concentration.

The encouraging results obtained on subcellular systems, prompted us to try similar experiments on whole cells.

Figure 5:
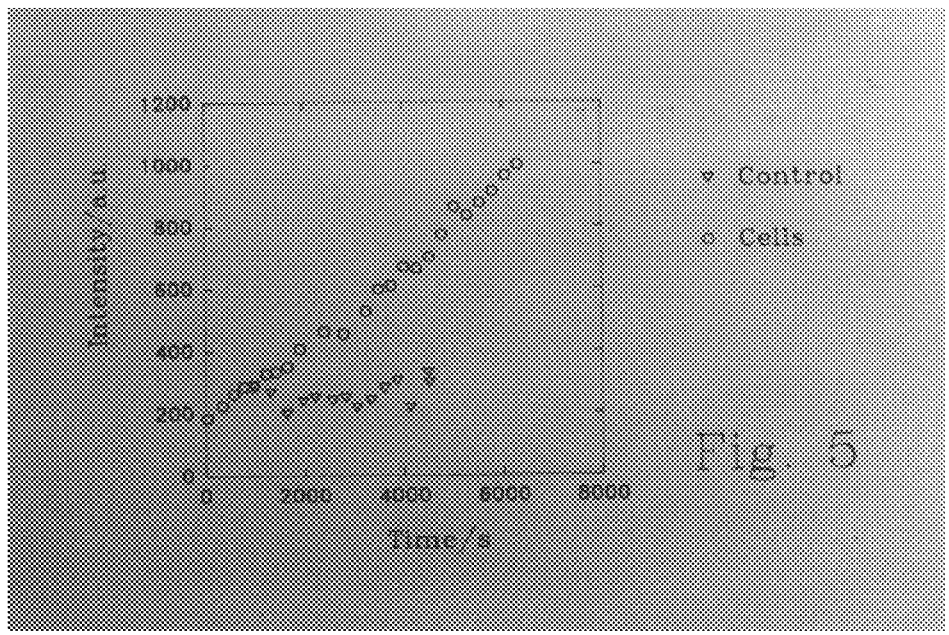

The liver epithelial cell line C2.8 was incubated in a nutrient medium (DMEM supplemented with 20% fetal calf serum, 10% trypticase soy broth, 50 U/ml penicillin and 50 μm/ml streptomycin) in the presence of 1 mM hydroxylamine. FIG. 5 shows that cell induced oxidation of the hydroxylamine takes place and therefore that this compound is lipophilic enough to cross the cell membrane.

These experiments demonstrate that the current hydroxylamine is a good probe for determining the rate of superoxide production in biological systems, and (miming the antioxidant activity) can easily be used as alternative toD antioxidant enzymes (i.e. superoxide dismutase, SOD).

The generation of the nitroxide radical, giving origin to strong EPR signals can be presumably ascribed to the following reaction mechanisms:

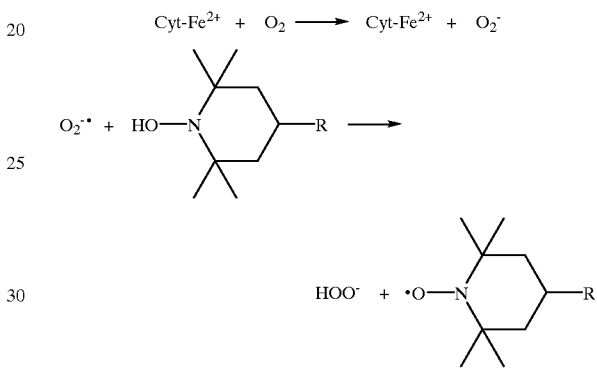

Figure 6:
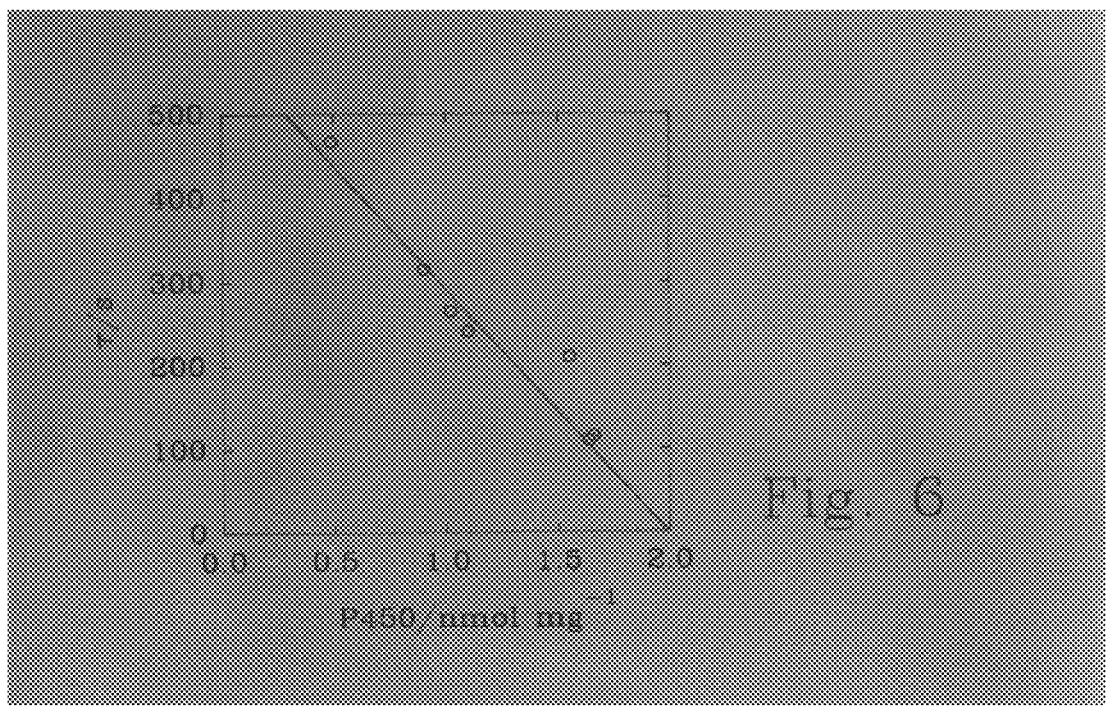

Disappearance of the previously formed nitroxide is due to high peroxide formation induced by P450. This interpretation is in accordance with the results obtained in the presence of vitamin E. In fact, vitamin E acts as a block to the decrease in nitroxide kinetics. It is also possible for it to react directly with the superoxide, and this accounts for the reduction of the rate of nitroxide formation observed with increasing vitamin E concentrations. Finally, it is important to note that the amount of P450 and the rate of nitroxide formation are directly proportional, a good correlation parameter (r=0.9) is represented by τ time at which the EPR signal reaches its maximum. In FIG. 6, τ is plotted versus P450 concentration in the various induced fractions and controls.

Finally, by intraperitoneal (i.p.) administration at a dosage of 100 mg/kg on percentage basis in sunflower seed oil, and collecting in 2 hours time intervals the urines of animals placed in suitable metabolic cages, superoxide formed in vivo was successfully detected in toto. This longed for (EPR-Whole-Body) technique thus allowed the determination of oxidative stress in control animals which were given the various P450 inducers according to dosages listed on page 17. As inferred from FIG. 7, independently of the used enzymatic inducer, similarly to the results obtained in vitro, the nitroxide formation markedly increases in inductive situations in comparison to controls.

Continued exposure to the multiple xenobiotics which are potential inducers of all those P450 isoforms causes an inductive status (at high carcinogenic risk) in man. The "unspecific" production of superoxide by the different P450 isoforms, particularly evident under induction, demonstrates the importance of detecting such a status by determining said superoxide in man.

It is not particularly important if induction results from exposure to work environments (thinners, dioxine, etc.), certain styles of living (cigarette smoke, alcohol, etc.), pharmacological treatments (barbiturates, Ca-antagonists, atc.), diet (cauliflower, Brussel sprouts, etc.) or if it is a result of constitution as with high metabolizers (genetic polymorphisms). In any case, in fact, since the oxidative stress resulting therefrom (high superoxide production) acts at every level of the carcinogenic process (starting, promotion, progress), it leads the individual to high neoplasty risk. Said oxidative stress is also at a high risk with regards to all those pathologies dependent on excess production of free radicals.

As it is inferred from the results, there is a correlation between the (unspecific) induction of P450 function and the production of superoxide. Thus, it will be possible to carry out the detection of induction, generally from the oxidative stress level, in man, after administering hydroxylamine according to this invention, indirectly by detecting the superoxide itself, or better the corresponding nitroxide, directly in urines, by EPR analysis.

A high nitroxide level is an index of high carcinogenic risk and pathologies relevant to excess production of free radicals.

Figure 7:
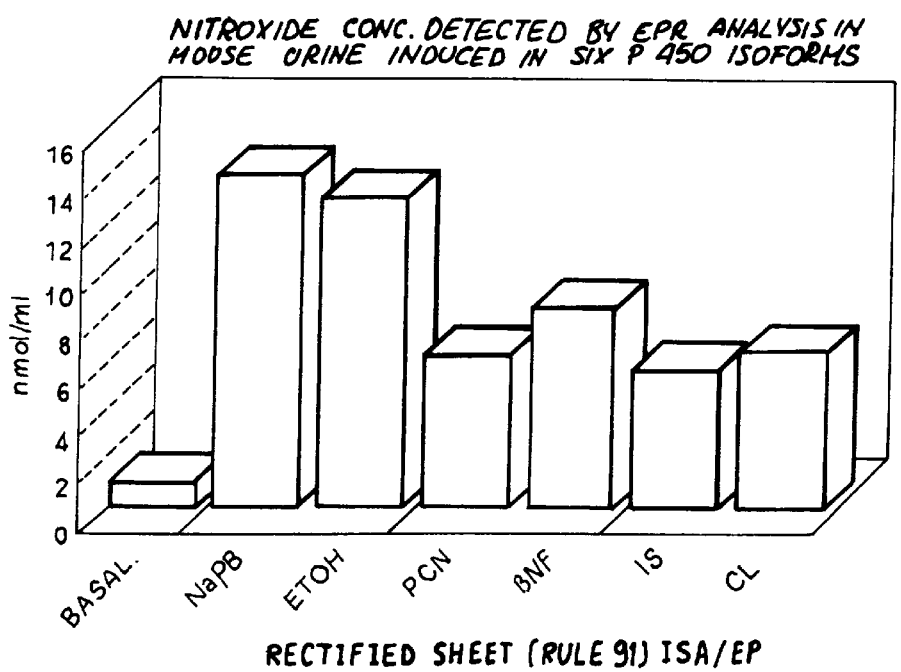

FIG. 7 refers to nitroxide concentration detected by EPR analysis in mouse urine, induced in 1A1, 1A2, 2B1, 2E1, 3A, 4A P450 isoforms.

In accordance with the present invention, a method of cosmetic treatment is provided, which comprises the step of topical administration of the compound described heretofore and defined in the appended claims.

A diagnostic method is also provided, which comprises the step of administering to a patient the compound described heretofore and defined in the appended claims, then analyzing a body fluid of the patient such as urine.

A food preservation method, for preventing food from becoming rancid, is also provided by the present invention. The method comprises the step of adding to food to be preserved, a compound as described heretofore and as defined in the appended claims.

The present invention also provides a method for preventing deterioration of a cosmetic product. The method comprises the step of adding to a cosmetic product, a compound as described heretofore and as defined in the appended claims.

A method for preventing deterioration of organic matter susceptible to oxidation, is also provided by the present invention. The method comprises the step of adding to the organic matter susceptible to oxidation, a compound as described heretofore and as defined in the appended claims.

We claim:

1. A pharmaceutical composition for attenuation of production of oxygen free radicals in humans comprising an antioxidant effective amount of a compound having the formula:

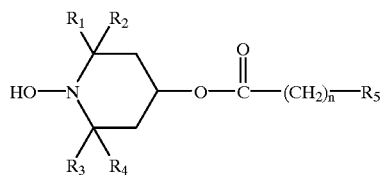

wherein $R_1$, $R_2$, $R_3$, $R_4$ are independently selected from:
hydrogen,
alkyl of from one to twelve carbon atoms,
alkenyl of from two to twelve carbon atoms,
alkynyl of from two to twelve carbon atoms, or
$R_1$ and $R_2$ together are tetramethylene or pentamethylene;
$R_5$ is hydrogen,
alkyl of from one to twelve carbon atoms,
cycloalkyl of from three to eight carbon atoms,
alkenyl of from two to twelve carbon atoms,
alkynyl of from two to twelve carbon atoms, or

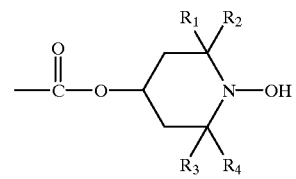

wherein $R_1$, $R_2$, $R_3$, $R_4$ are as defined above and n is an integer of from one to thirty;

in association with a physiologically acceptable carrier.

2. A pharmaceutical composition according to claim 1, wherein $R_1$, $R_2$, $R_3$, $R_4$ are independently an alkyl of from one to six carbon atoms and $R_5$ is

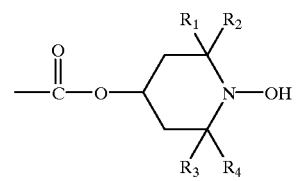

wherein $R_1$, $R_2$, $R_3$, $R_4$ are independently an alkyl of from one to six carbon atoms and n is an integer of from two to fourteen.

3. A pharmaceutical composition according to claim 1, wherein $R_1$, $R_2$, $R_3$, $R_4$ are independently an alkyl of from one to three carbon atoms, $R_5$ is

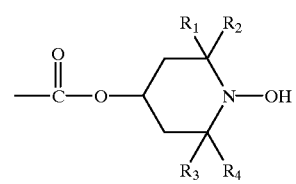

wherein $R_1$, $R_2$, $R_3$, $R_4$ are independently an alkyl of from one to three carbon atoms, and n is an integer of from six to ten.

4. A pharmaceutical composition according to claim 1, wherein said compound is of the formula:

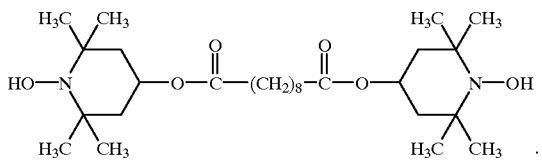

5. A pharmaceutical composition according to claim 1, wherein said physiologically acceptable carrier is a solid carrier for topical administration.

6. A nutritional composition having anti-free radical activity comprising an antioxidant effective amount of a compound having the formula:

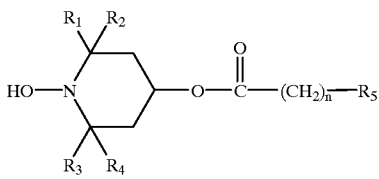

wherein $R_1$, $R_2$, $R_3$, $R_4$ are independently selected from the group consisting of:
hydrogen,
alkyl of from one to twelve carbon atoms,
alkenyl of from two to twelve carbon atoms, and
alkynyl of from two to twelve carbon atoms, or
$R_1$ and $R_2$ together are tetramethylene or pentamethylene;
$R_5$ is selected from the group consisting of hydrogen,
alkyl of from one to twelve carbon atoms,
cycloalkyl of from three to eight carbon atoms,
alkenyl of from two to twelve carbon atoms,
alknyl of from two to twelve carbon atoms, and

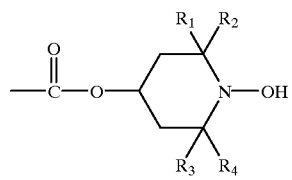

wherein $R_1$, $R_2$, $R_3$, $R_4$ are as defined above, and
n is an integer of from one to thirty;
in association with a food product.

7. A method for attenuation of production of oxygen free radicals comprising the administration to a human of an antioxidant effective amount of a compound of the formula:

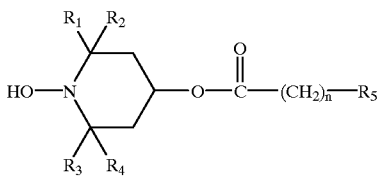

wherein $R_1$, $R_2$, $R_3$, $R_4$ are independently selected from:
hydrogen,
allyl of from one to twelve carbon atoms,
alkenyl of from two to twelve carbon atoms,
alkynyl of from two to twelve carbon atoms, or
$R_1$ and $R_2$ together are tetramethylene or pentamethylene;
$R_5$ is hydrogen,
alkyl of from one to twelve carbon atoms,
cycloalkyl of from three to eight carbon atoms,
alkenyl of from two to twelve carbon atoms,
alkynyl of from two to twelve carbon atoms, or

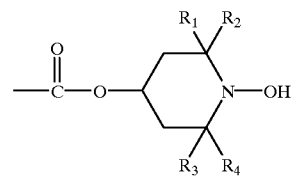

wherein $R_1$, $R_2$, $R_3$, $R_4$ are as defined above and n is an integer of from one to thirty;
in association with a physiologically acceptable carrier.

8. Method according to claim 7, wherein said administration is a topical administration.

9. Method according to claim 7, wherein said administration is an oral administration.

10. A method for detecting a cellular oxidative stress level in humans comprising administering an antioxidant effective amount of a compound of the formula:

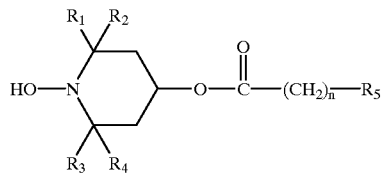

wherein $R_1$, $R_2$, $R_3$, $R_4$ are independently selected from:
hydrogen,
alkyl of from one to twelve carbon atoms,
alkenyl of from two to twelve carbon atoms,
alkynyl of from two to twelve carbon atoms, or
$R_1$ and $R_2$ together are tetramethylene or pentamethylene;
$R_5$ is hydrogen,
alkyl of from one to twelve carbon atoms,
cycloalkyl of from three to eight carbon atoms,
alkenyl of from two to twelve carbon atoms,
alkynyl of from two to twelve carbon atoms, or

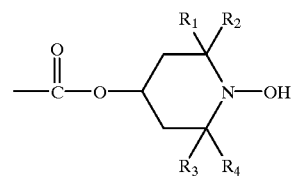

wherein $R_1$, $R_2$, $R_3$, $R_4$ are as defined above and n is an integer of from one to thirty;
in association with a physiologically acceptable carrier and then detecting the presence of superoxide anions.

11. Method according to claim 10, wherein the superoxide anions are detected by EPR analysis.

* * * * *